United States Patent
Wheatley

(10) Patent No.: US 10,470,656 B2
(45) Date of Patent: Nov. 12, 2019

(54) IMAGING PROBES AND ASSOCIATED DEVICES, SYSTEMS, AND METHODS UTILIZING ELECTROACTIVE POLYMER ACTUATORS

(71) Applicant: Novartis AG, Basel (CH)

(72) Inventor: Barry L. Wheatley, Oceanside, CA (US)

(73) Assignee: Novartis AG, Basel (CH)

( * ) Notice: Subject to any disclaimer, the term of this patent is extended or adjusted under 35 U.S.C. 154(b) by 326 days.

(21) Appl. No.: 14/137,252

(22) Filed: Dec. 20, 2013

(65) Prior Publication Data

US 2015/0173604 A1    Jun. 25, 2015

(51) Int. Cl.
| | | |
|---|---|---|
| *A61B 5/05* | (2006.01) | |
| *A61B 3/10* | (2006.01) | |
| *A61B 5/06* | (2006.01) | |
| *A61B 3/12* | (2006.01) | |
| *G02B 6/36* | (2006.01) | |
| *G01B 9/02* | (2006.01) | |
| *G02B 23/26* | (2006.01) | |

(Continued)

(52) U.S. Cl.
CPC ............ *A61B 3/102* (2013.01); *A61B 3/1208* (2013.01); *A61B 5/066* (2013.01); *G01B 9/0205* (2013.01); *G01B 9/02091* (2013.01); *G02B 6/3624* (2013.01); *G02B 23/26* (2013.01); *G02B 26/103* (2013.01); *A61B 5/0084* (2013.01)

(58) Field of Classification Search
CPC ..... A61B 3/102; A61B 5/0082; A61B 3/1208; A61B 5/0084; G01B 9/0205; G01B 9/02091; G02B 23/26; G02B 26/103; G02B 6/3624
See application file for complete search history.

(56) References Cited

U.S. PATENT DOCUMENTS

| | | |
|---|---|---|
| 2002/0089259 A1 | 6/2002 | Iino et al. |
| 2003/0048455 A1 | 3/2003 | Fleming et al. |
| | (Continued) | |

FOREIGN PATENT DOCUMENTS

| | | | |
|---|---|---|---|
| WO | WO 2007/029275 | 3/2007 | |
| WO | WO2012/166116 A1 * | 6/2012 | ............... A61B 5/00 |

OTHER PUBLICATIONS

International Search Report and Written Opinion issued for PCT/US2014/068894 dated Mar. 2, 2015, 12 pgs.

(Continued)

*Primary Examiner* — Jonathan Cwern

(57) ABSTRACT

Devices, systems, and methods that utilize electroactive polymer actuators to impart motion to an optical fiber positioned within an imaging probe are provided. In some embodiments, an ophthalmic imaging apparatus comprises an optical probe having a handle sized and shaped for handheld grasping by a user; and a cannula coupled to the handle, the cannula sized and shaped for insertion into an eye to be treated; an optical fiber positioned at least partially within the optical probe, the optical fiber configured to receive an imaging light from an imaging light source and guide the imaging light to an optical element positioned within the cannula of the optical probe; and an actuator system configured to impart motion to the optical fiber, the actuator system including an electroactive polymer (EAP) actuator positioned within the optical probe.

32 Claims, 5 Drawing Sheets

(51) Int. Cl.
 *G02B 26/10* (2006.01)
 *A61B 5/00* (2006.01)

(56) References Cited

U.S. PATENT DOCUMENTS

| | | |
|---|---|---|
| 2003/0119030 A1 | 6/2003 | Zilber |
| 2004/0070316 A1 | 4/2004 | Neubauer et al. |
| 2005/0078910 A1 | 4/2005 | Hickingbotham |
| 2006/0170930 A1* | 8/2006 | Li ................... A61B 5/0059 356/479 |
| 2008/0249369 A1 | 10/2008 | Seibel et al. |
| 2008/0265178 A1* | 10/2008 | Johnston ............ G02B 26/10 250/492.1 |
| 2009/0049944 A1 | 2/2009 | Kiesewetter et al. |
| 2009/0293664 A1 | 12/2009 | Aabloo et al. |
| 2010/0228124 A1 | 11/2010 | Brennan et al. |
| 2011/0122203 A1 | 5/2011 | McAvoy et al. |
| 2011/0122366 A1 | 5/2011 | Smith |
| 2012/0310042 A1* | 12/2012 | Joos ................... A61B 18/20 600/108 |
| 2013/0335354 A1* | 12/2013 | Zellers ............... H01L 41/0926 345/173 |

OTHER PUBLICATIONS

Kornbluh, Roy, et al., "Dielectric Elastomer Actuators: Fundamentals," in "Biomedical Applications of Electroactive Polymer Actuators," Frederico Carpi, et al., editors, West Sussex, UK: Wiley, 2009, pp. 387-393 and 446-448.

Shahinpoor, Moshen, "Artificial Muscles—Applications of Advanced Polymeric Nanocomposites," New York: CRC Press, 2007, pp. 1-8.

* cited by examiner

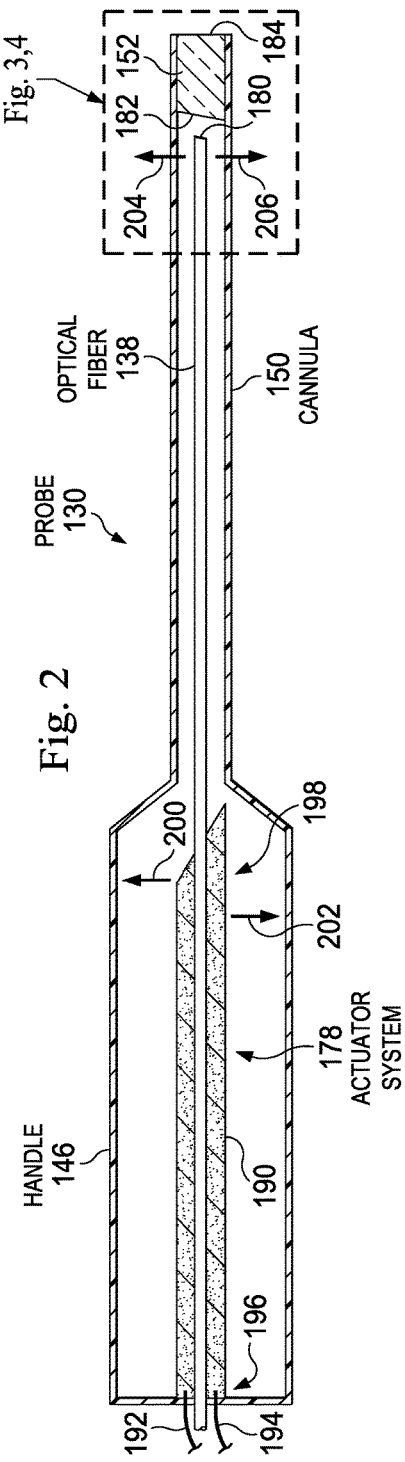
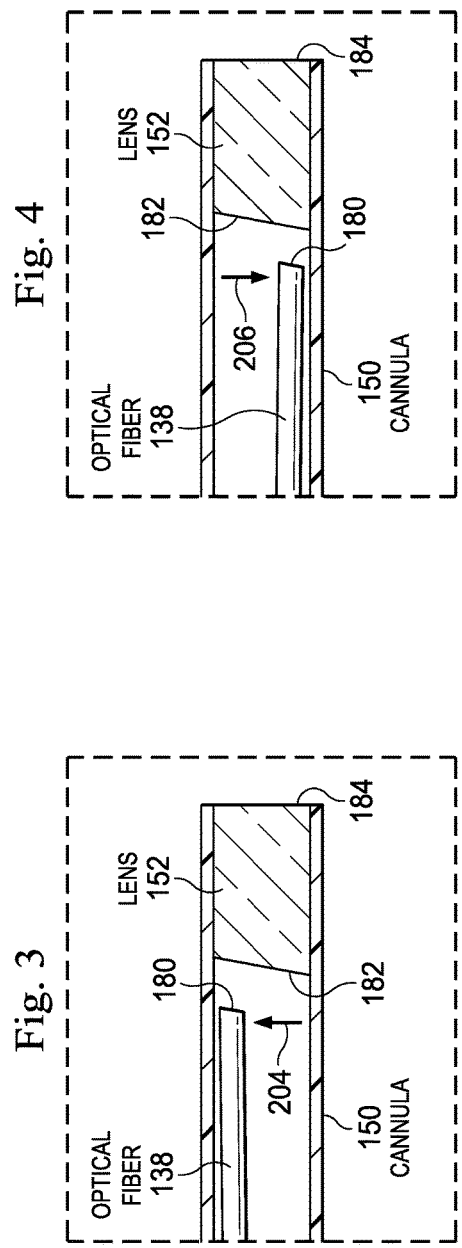

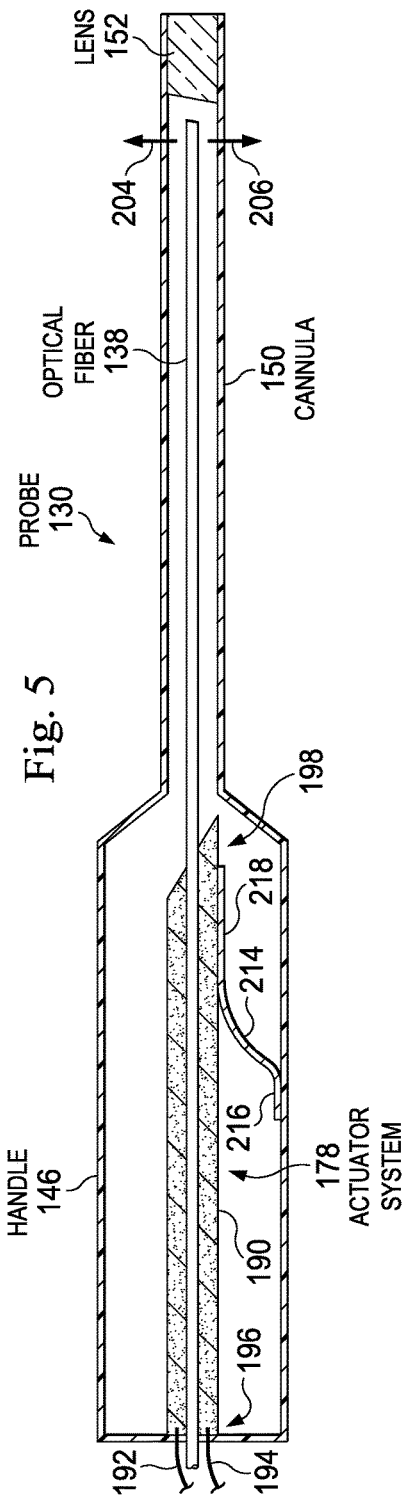
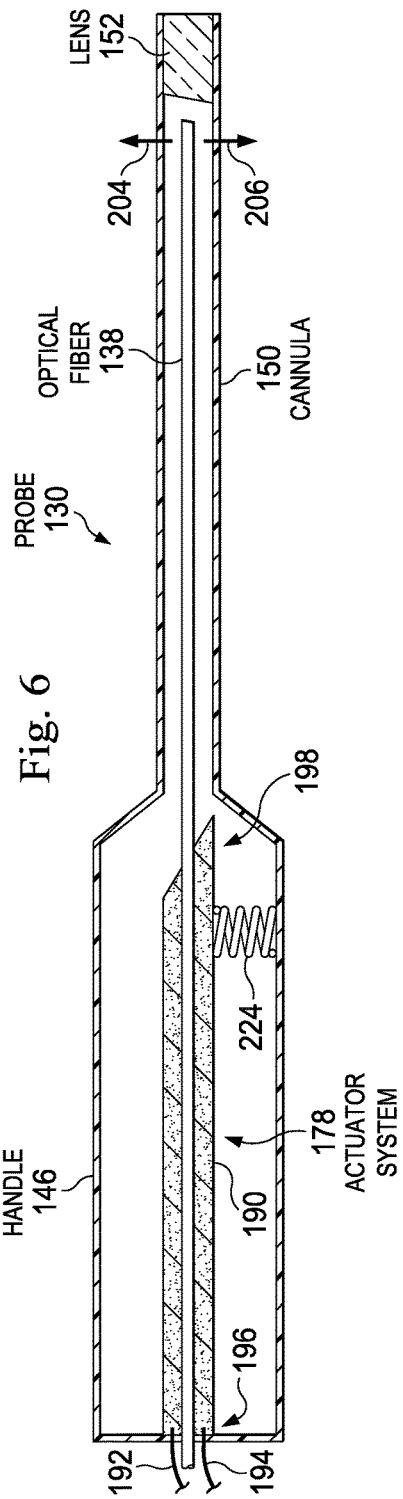

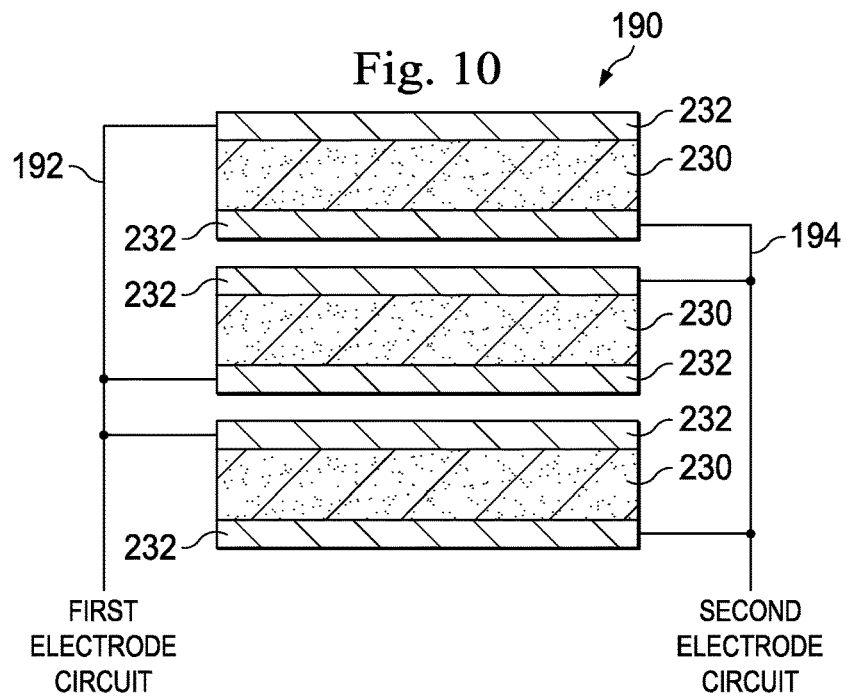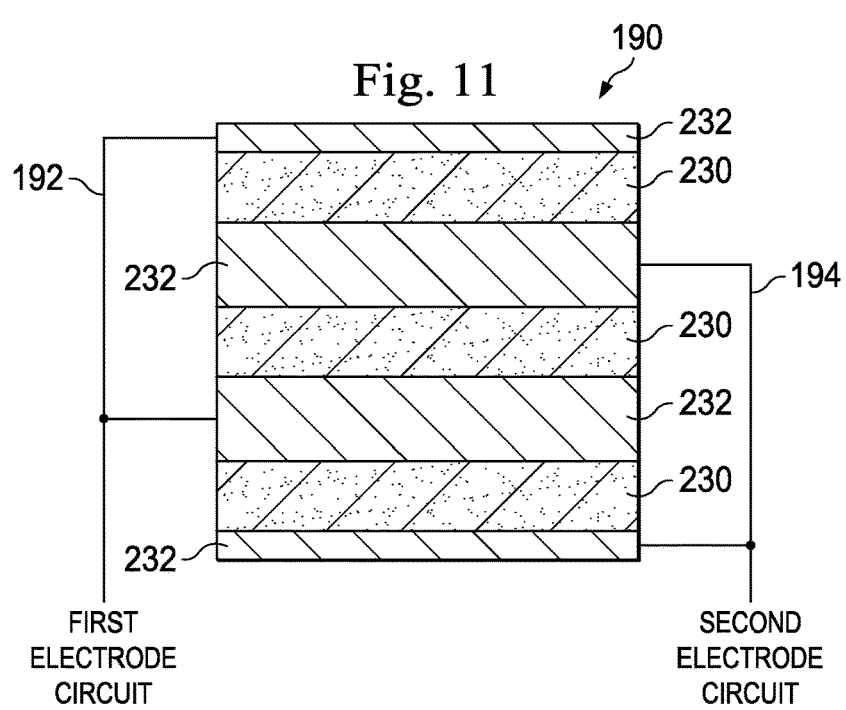

IMAGING PROBES AND ASSOCIATED DEVICES, SYSTEMS, AND METHODS UTILIZING ELECTROACTIVE POLYMER ACTUATORS

TECHNICAL FIELD

Embodiments disclosed herein can be related to devices, systems, and methods for scanning tissue with an optical coherence tomography (OCT) probe, and more particularly, to devices, systems, and methods that utilize an OCT probe having a displaceable fiber for ophthalmic imaging.

BACKGROUND

Optical Coherence Tomography (OCT) systems can be used to capture and generate images of patient tissue layers. These systems often include OCT probes that can invasively penetrate tissue to obtain visualization of tissue within a patient. In ophthalmology, OCT probes can be used to obtain detailed images of tissue about the eye or even forming a part of the eye, such as the retina.

In use, an optical light beam can be directed through the probe at the tissue. A small portion of this light reflects from sub-surface features of the tissue and can be collected through the same probe. Most of the light diffusely scatters at large angles, instead of being reflected. In conventional imaging, this diffusely scattered light contributes background noise that obscures an image. However, in OCT, a technique called interferometry records the optical path lengths of received photons, and provides data that rejects most of the photons that scatter multiple times before detection. This can result in clearer images that extend in the depth of the tissue.

The OCT probes often include a projecting cannula that can invasively penetrate patient tissue. The probe can scan tissue by refracting the optical light beam through a lens disposed at an end of the cannula. A scan can include moving an optical fiber back and forth within the cannula to direct the light beam through the lens and at the tissue at different angles. The length and small diameter of the cannula can make it difficult to move the fiber back and forth within the cannula. Further, the small amount of available space within the probe can limit the types of actuators that can be utilized. Further still, the OCT probes and associated systems should be capable of being manufactured in a cost-effective manner, which includes the ability to make the probe as a disposable, one-time use device in some implementations.

Accordingly, there remains a need for improved devices, systems, and methods that utilize an OCT probe having a displaceable fiber for ophthalmic imaging, including ophthalmic OCT probes that address one or more of the needs discussed above.

SUMMARY

Embodiments disclosed herein can be related to devices, systems, and methods that utilize an electroactive polymer (EAP) actuator to impart motion to an optical fiber positioned within an imaging probe.

Consistent with some embodiments, an ophthalmic imaging apparatus can be provided. The ophthalmic imaging apparatus can include an optical probe having a handle sized and shaped for handheld grasping by a user; and a cannula coupled to the handle, the cannula sized and shaped for insertion into an eye to be treated; an optical fiber positioned at least partially within the optical probe, the optical fiber configured to receive an imaging light from an imaging light source and guide the imaging light to an optical element positioned within the cannula of the optical probe; and an actuator system configured to impart motion to the optical fiber, the actuator system including an EAP actuator positioned within the optical probe.

Consistent with some embodiments, an ophthalmic imaging system can be provided. The system can include an imaging light source configured to generate an imaging light; an optical guide in optical communication with the imaging light source, the optical guide configured to receive the generated imaging light from the imaging light source; and a probe in optical communication with the optical guide, the probe including a handle sized and shaped for handheld grasping by a user; and a cannula coupled to the handle, the cannula sized and shaped for insertion into an eye to be treated; an optical fiber positioned at least partially within the optical probe, the optical fiber configured to receive the imaging light from the optical guide and guide the imaging light to an optical element positioned within the cannula of the optical probe; and an actuator system configured to impart motion to the optical fiber, the actuator system including an EAP actuator positioned within the optical probe.

Consistent with some embodiments, method of imaging an ophthalmic target with an imaging probe can be provided. The method can include guiding an imaging light to an optical fiber positioned within a cannula of the imaging probe with an optical guide; focusing the imaging light onto the ophthalmic target with an optical element positioned within the cannula of the imaging probe; and scanning the focused imaging light through a scanning pattern by moving a distal end of the optical fiber by applying an electrical stimulation to an EAP actuator positioned within the imaging probe.

Additional aspects, features, and advantages of the present disclosure will become apparent from the following detailed description.

BRIEF DESCRIPTION OF THE DRAWINGS

FIG. 2 provides a stylized illustration of a cross-sectional view of an imaging probe.

FIG. 3 provides a stylized illustration of a cross-sectional view of a distal portion of the imaging probe of FIG. 2 showing an optical fiber of the imaging probe in a first position.

FIG. 4 provides a stylized illustration of a cross-sectional view of the distal portion of the imaging probe of FIG. 2, similar to that of FIG. 3 but showing the optical fiber in a second position.

FIG. 5 provides a stylized illustration of a cross-sectional view of an imaging probe.

FIG. 6 provides a stylized illustration of a cross-sectional view of an imaging probe.

FIG. 10 provides a stylized illustration of a cross-sectional view of an electroactive polymer actuator.

FIG. 11 provides a stylized illustration of a cross-sectional view of an electroactive polymer actuator.

Figure 1:
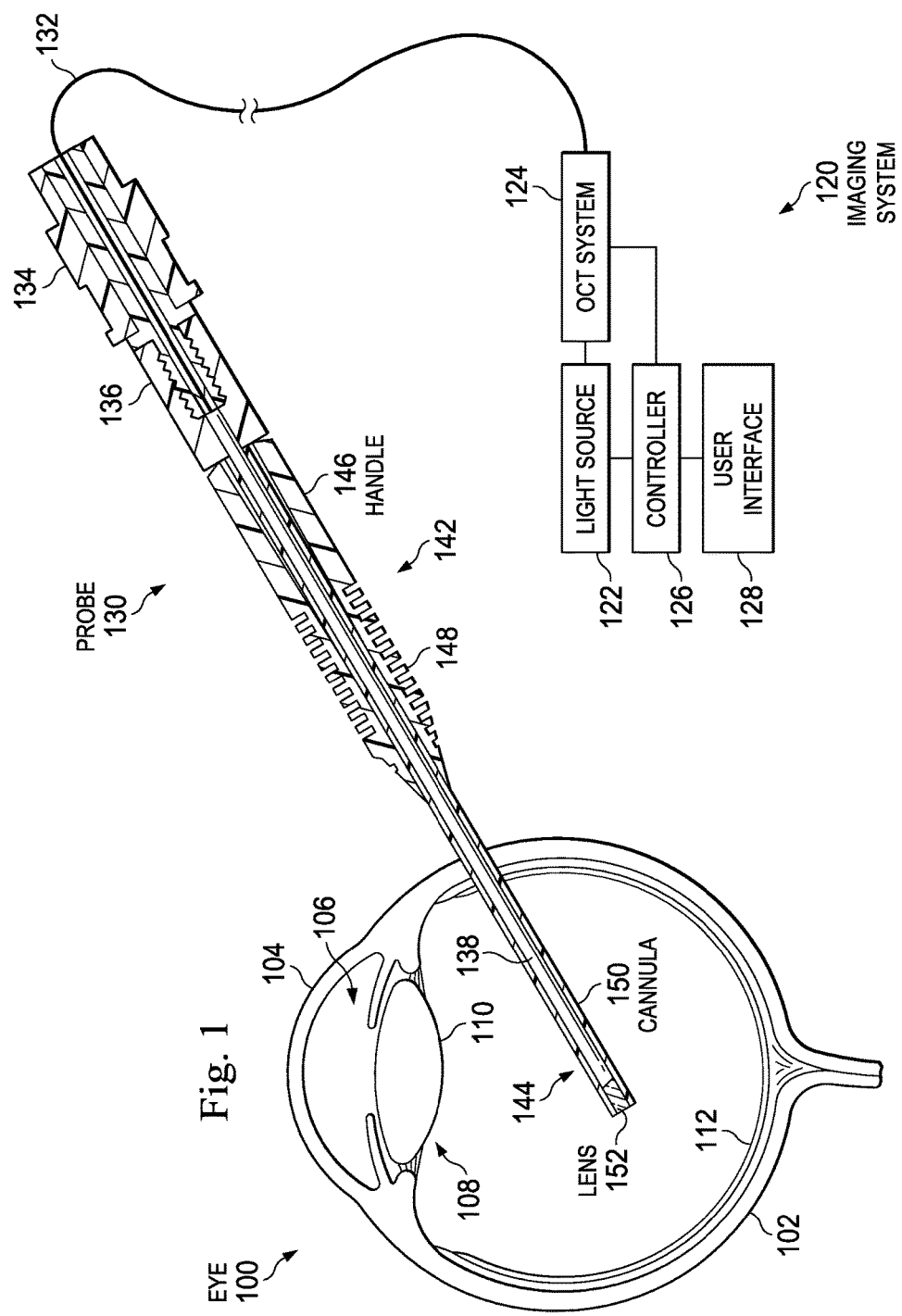
FIG. 1 provides a diagrammatic schematic view of an eye under treatment and an OCT imaging system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The probe can include a cannula configured to invasively penetrate patient tissue, such as the globe of an eye. The cannula can house a lens and an optical fiber. The fiber can direct light through the lens and capture reflected light that passes back through the lens. To obtain a scan of an area or a line of tissue, rather than merely a point, the fiber can be moved within the cannula relative to the lens to cause the light emerging from the lens to scan across the desired pattern. Because the cannula that penetrates the patient tissue can be desirably small in cross-section, moving the fiber within the cannula can be difficult. The small amount of available space within the probe can limit the types of actuators that can be utilized to impart movement to the fiber. In some instances it can be desirable to manufacture the probe, or at least a portion thereof, as a disposable component, which requires product designs having cost-effective manufacturing techniques.

Exemplary aspects described herein utilize a technique of moving at least a distal end of the fiber within the cannula using an actuator system positioned at least partially within the probe that overcomes one or more of the problems or limitations of previous approaches. The actuator system can include an electroactive polymer (EAP) actuator. Such EAP actuators can be controlled by electrical stimulation, where the electrical stimulation can include applying a current, voltage or electric field. The EAP actuator can be positioned outside the cannula, such as in a handle of the probe, or inside the cannula. The distal end of the fiber can be moved by electrically activating the EAP actuator. The fiber can be coupled to the EAP actuator such that the movement of the EAP actuator results in a corresponding movement of the distal end of the fiber. As a result, embodiments of the present disclosure (1) can be configured for use within the limited space available within an OCT probe, (2) can amplify the motion of the distal end of the fiber relative to the motion of the EAP actuator, (3) can avoid the need for an actuator system that relies upon an interaction of mechanical components that can require very precise manufacturing tolerances, be difficult to assemble, and have a tendency to break at the sizes necessary for use in an OCT probe, (4) can impart repeatable motion to the optical fiber of the OCT probe suitable for optical scanning, and (5) can be manufactured in a cost-effective manner.

FIG. 1 provides a diagrammatic schematic view of an eye 100 under treatment and an OCT imaging system 120. The eye 100 can include sclera 102, a cornea 104, an anterior chamber 106, and a posterior chamber 108. A capsular bag 110 can be positioned in the posterior chamber 108. The eye 100 can include a retina 112. As discussed in greater detail below, the imaging system 120 can be configured to image portions of the eye 100, such as the retina 112. The imaging system 120 can include a light source 122, an optical coherence tomography (OCT) system 124, a controller 126, a user interface 128, and a probe 130. The light source 122 can be configured to provide imaging light that will be directed onto the target biological tissue by the probe 130. The light source 122 can be made up of super-luminescent diodes, ultra-short pulsed lasers, or supercontinuum lasers that provide relative long wavelength light, such as between 700 nm and 1400 nm, between 900 nm and 1200 nm, or between 1000 nm and 1100 nm. Imaging light reflected from the target biological tissue and captured by the probe 130 can be utilized to generate images of the target biological tissue.

The OCT system 124 can be configured to split the imaging light received from the light source 122 into the imaging beam that can be directed onto the target biological tissue by the probe 130 and a reference beam that can be directed onto a reference mirror. The OCT system 124 can be a spectral domain or a time domain system. The OCT system 124 can be further configured to receive the imaging light reflected from the target biological tissue and captured by the probe 130. The interference pattern between the reflected imaging light and the reference beam can be utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the probe 130, and for executing and performing functions and processes to carry out an OCT imaging procedure. For example, the controller 126 can be configured to control an actuation system of probe 130 configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller can be positioned within a console communicatively coupled to the user interface 128. The user interface 128 can be carried on or form part of the console. Further, the user interface 128, or at least part(s) thereof, can be separate from the console. The user interface 128 can include a display configured to present images to a user or a patient, and display tissue scanned by the probe 130 during an OCT imaging procedure. The user interface 128 can also include input devices or systems, including by way of non-limiting example, a keyboard, a mouse, a joystick, a touchscreen, dials, and buttons, among other input devices.

The probe 130 can be in optical communication with OCT system 124. In that regard, the probe 130 can be configured to present light from the light source 122 that passes through OCT system 124 onto the target biological tissue for the purpose of imaging the tissue. Further, the probe can be in electrical communication with the controller 126. In that regard, the controller 126 can control an actuation system of the probe 130 via electrical signals sent to the probe 130 in order to cause the actuation system to scan the imaging beam across the target biological tissue. A cable 132 can connect the probe 130 to the OCT system 124 and/or the controller 126. In that regard, cable 132 can include optical fiber(s), electrical conductor(s), insulator(s), shield(s), and/or other features configured to facilitate optical and/or electrical communication between the probe 130 and the OCT system 124 and/or the controller 126. Further, the cable 132 can include multiple, separate cables. For example, in some instances an optical cable connects the probe 130 to OCT system 124 and a separate electrical cable connects the probe 130 to controller 126.

In the illustrated embodiment, the cable 132 terminates in a connector 134 configured to facilitate removable coupling of the probe 130 to the cable 132. The connector 134 can be configured to selectively engage with a connector 136 associated with the probe 130 to facilitate mechanical, optical, and/or electrical coupling of the probe 130 to the cable 132. For example, an optical fiber 138 extending along the length of the probe 130 can be optically coupled to the OCT system 124 via the coupling of the connectors 134 and 136. The optical fiber 138 can be a single fiber or a fiber bundle. The connector 136 can be configured to threadingly engage with the connector 134. However, any type of selective engagement feature(s) or connectors can be utilized to couple the probe 130 to the cable 132, including without limitation press fit, luer lock, threads, and combinations thereof, among other connection types. The selective engagement of the connector 136 with the connector 134 allows the entire probe 130 to be a disposable component configured for use in a single procedure, while the connector 134 and cable 132 can be reusable components that can be sterilized (e.g., using autoclave procedures) and used in multiple procedures.

The probe 130 can be sized and shaped to be handled by a surgeon and to protrude into a body of the patient. The probe 130 can include a proximal portion 142 and a distal portion 144. The proximal portion 142 can include a handle 146 sized and shaped for handheld grasping by a user. For example, the handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the user can control the position of the distal portion 144 of the probe 130 by maneuvering the handle 146 such that the imaging light beam can be directed towards the target biological tissue.

The distal portion 144 of the probe 130 can be sized and shaped for insertion into the eye 100 to be treated. In the illustrated embodiment of FIG. 1, the distal portion 144 of the probe 130 includes a cannula 150. The cannula 150 can be sized and shaped for insertion through the sclera 102 of the eye 100 to facilitate imaging the retina 112. The cannula 150 can be integrally formed with the handle 146. Alternatively, the cannula 150 and the handle 146 can be separate components fixedly secured to one another. An optical element 152, such as a lens, can be secured within the distal end of the cannula 150. The optical element 152 can be configured to focus the imaging light onto the target biological tissue, such as the retina 112. The optical element 152 can be a gradient index (GRIN) lens or a regular lens. Depending upon the embodiment, the gradient index may be spherical, axial, or radial. The optical element 152 can also be a spherical lens. Other lens shapes may be used.

As will be discussed in greater detail below, the optical fiber 138 can be moved with respect to the optical element 152 by an actuator system disposed within the probe 130 to cause the imaging beam—as focused by the optical element 152—to scan across a portion of the target biological tissue. FIGS. 3, 6, 7, and 9 described below illustrate various embodiments of actuator systems in accordance with the present disclosure. In that regard, the actuator systems of the present disclosure can be positioned within the handle 146, within the cannula 150, and/or combinations thereof to move the optical fiber 138 across a desired scan pattern.

The distance of the focal point of the imaging beam from the distal end of the probe 130 can be determined by the optical element 152. Accordingly, in some instances the focal power of the optical element 152 can be selected to have a focus depth corresponding to likely distance of the distal end of the probe 130 from the target biological tissue during use. For example, in some implementations of the probe 130 for retinal imaging, the focal power of the optical element 152 can be selected such that the focal point of the imaging beam can be between 1 mm and 20 mm, between 5 mm and 10 mm, between 7 mm and 8 mm, or approximately 7.5 mm beyond the distal end of the probe 130.

FIG. 2 provides a stylized illustration of a cross-sectional view of an embodiment of probe 130. As shown, the optical fiber 138 can extend along the length of the probe 130 through the handle 146 and the cannula 150. In the illustrated embodiment, an actuator system 178 can be positioned within the handle 146. The actuator system 178 can be configured to impart motion to the optical fiber 138 such that a distal end 180 of the optical fiber 138 moves with respect to the cannula 150 and the optical element 152 fixedly secured to the cannula. More specifically, the distal end 180 of the optical fiber 138 can be moved with respect to the optical element 152 to scan the imaging beam across a desired pattern with respect to the target biological tissue.

The optical element 152 can be configured to focus the imaging beam received from the optical fiber 138 onto the target biological tissue. In that regard, the optical element 152 can include a proximal face 182 and a distal face 184. The imaging beam can enter the optical element 152 through the proximal face 182 and leaves the optical element 152 through the distal face 184. As shown, the proximal face 182 of the optical element 152 can extend at an oblique angle with respect to the longitudinal axis of the cannula 150. By having the proximal face 182 oriented at an oblique angle, the amount of reflection resulting from the imaging beam entering the optical element 152 can be reduced. In other embodiments, the proximal face 182 extends perpendicular to the longitudinal axis of the cannula 150.

The distal end 180 the optical fiber 138 can be spaced from the proximal face 182 of the optical element 152. In that regard, the spacing between the distal end 180 of the optical fiber 138 and the proximal face 182 of the optical element 152 can be selected to achieve a desired optical performance (e.g., focal distance, focus size, etc.). The spacing between the distal end 180 of the optical fiber 138 and the proximal face 182 of the optical element 152 can also be selected to allow a desired range of motion of the optical fiber 138 within the cannula 150 without physically contacting the optical element 152. The optical element 152 can be mechanically coupled to the distal end 180 of the optical fiber 138 such that the optical element 152 moves with the distal end 180 of the optical fiber 138.

The actuator system 178 can be configured to impart motion to the optical fiber 138 such that the distal end 180 of the optical fiber 138 can be moved with respect to the optical element 152 to scan the imaging beam across a desired pattern with respect to the target biological tissue. The actuator system 178 can include an electroactive polymer (EAP) actuator 190 and electrical conductors 192, 194.

The EAP actuator 190 can utilize any suitable EAP. In general, EAPs can be materials that produce a strain when exposed to stimulation. The stimulation can include electrical stimulation, such as applying a current, voltage or electric field. The EAP can be an ionic EAP or a dielectric EAP. Ionic EAPs can respond to low voltages with high strain and produce low actuating forces. Some ionic EAPs can be utilized in a bath of ionic solution. In such instances, the probe 130 can include a reservoir, containment capsule, or other structure configured to hold the ionic solution and the EAP. Ionic EAPs can include, without limitation, electrorheological fluids, ionic polymer-metal composites, and stimuli-responsive gels. Dielectric EAPs can respond to high voltages with low strain and produce higher actuating forces. Dielectric EAPs can be kept dry, without the need for a solution bath. Dielectric EAPs can include, without limitation, ferroelectric polymers, electrostrictive graft polymers, and liquid crystalline polymers. As will be discussed below (for example, in the context of FIGS. 7 and 9-11), the EAP can form one or more layers of a sandwich structure. The sandwich structure can include EAP layer(s), electrically conductive layer(s), and/or insulating layer(s). Further, the EAP actuator 190 may include materials and/or features similar to those found in Carpi, Frederico, *Biomedical Applications of Electroactive Polymer Actuators*, West Sussex, UK: Wiley, 2009 or Shahinpoor, Moshen, *Artificial Muscles—Applications of Advanced Polymeric Nanocomposites*, New York: CRC Press, 2007, each of which is hereby incorporated by reference in its entirety.

A proximal section 196 of the EAP actuator 190 can be fixedly secured to a wall or other structure of handle 146, while a distal section 198 of the EAP actuator 190 can be movable with respect to the handle 146. More specifically, the actuator system 178 can be configured to cause the EAP actuator 190 to move with respect to the handle 146 in response to selective, electric energization via conductors 192, 194.

For example, by selectively applying a voltage to the EAP actuator 190 via electrical conductors 192, 194 the resulting current causes the distal section 198 of the EAP actuator 190 to be moved in either a first direction as indicated by arrow 200 or a second direction—opposite the first direction—as indicated by arrow 202. Accordingly, by controlling the magnitude and/or direction of the current, voltage or electric field applied to the EAP actuator 190 via electrical conductors 192, 194, the magnitude and direction of the resulting movement of the distal section 198 of the EAP actuator 190 can be controlled, which can be used to impart a desired motion profile to the distal end 180 of the optical fiber 138.

A proximal section of the optical fiber 138 can be secured to the EAP actuator 190 such that the optical fiber 138 moves with the distal section 198 of the EAP actuator 190 in response to the application of an electric voltage to the EAP actuator 190. The proximal section of the optical fiber 138 can be secured to the handle 146 adjacent to the proximal section 196 of the EAP actuator 190. The proximal section of the optical fiber 138 can be secured to the EAP actuator 190 using a suitable adhesive (e.g., glue, epoxy, etc.), mechanical connection, and/or combinations thereof.

As shown, the optical fiber 138 can be secured to the EAP actuator 190 such that the distal end 180 of the optical fiber 138 extends distally beyond the distal section 198 of the EAP actuator 190. In this manner, the distal end 180 of the optical fiber 138 can be cantilevered from the EAP actuator 190. As a result, the motion profile of the distal end 180 of the optical fiber 138 can be amplified relative to the motion profile of the distal section 198 of the EAP actuator 190. In other words, the movement of the distal end 180 of the optical fiber 138 can be greater than the corresponding movement of the distal section 198 of the EAP actuator 190. For example, when the distal section 198 of the EAP actuator 190 moves in the direction indicated by arrow 200, the distal end 180 of the optical fiber will move as indicated by arrow 204 a greater distance in the same direction. Similarly, when the distal section 198 of the EAP actuator 190 moves in the direction indicated by arrow 202, the distal end 180 of the optical fiber will move as indicated by arrow 206 a greater distance in the same direction. The ratio of the movement of the distal end 180 of the optical fiber 138 to the movement of the distal section 198 of the EAP actuator 190 can be between 1.01:1.0 and 10.0:1.0, between 1.1:1.0 and 5.0:1.0, or between 1.5:1.0 and 2.0:1.0. Accordingly, the resultant movement of the distal end 180 of the optical fiber 138 can be more than 1%, 10%, 20%, 50%, 100%, 500%, or 1000% greater than the movement of the distal section 198 of the EAP actuator 190.

In some instances, the motion profile of the distal end 180 of the optical fiber can simulate a lever arm action with a pivot point within the handle 146 of the probe 130. For example, the pivot point can be defined by the connection of the proximal section of the optical fiber 138 and/or the proximal section 196 of the EAP actuator 190 to the handle 146. In some instances, the EAP actuator 190 bends or curls during movement such that at least a portion of the EAP actuator 190 has an arcuate shape. For example, in some instances the distal section 198 of the EAP actuator 190 bends or curls relative to the fixed proximal section 196 during movement caused by electrically activating the EAP actuator 190.

In some embodiments, the EAP actuator 190 can be positioned at least partially in the cannula 150.

A stiffening member can be positioned adjacent to the optical fiber 138. The stiffening member can be formed of a material more rigid than the optical fiber 138. For example, the stiffening member can be formed of metal, hard plastic, ceramic, other suitable materials, and/or combinations thereof. The stiffening member can be a cylindrical tube positioned around a portion of the optical fiber 138. The stiffening member can also be a planar or arcuate plate structure extending around only a portion of the optical fiber 138. In that regard, the stiffening member can be configured to add rigidity to a portion of optical fiber 138 within an interior of the probe 130. The stiffening member can extend longitudinally along at least a portion of the optical fiber 138 such that the stiffening member extends entirely within the handle 146, extends entirely within the cannula 150, or partially extends in both the handle 146 and the cannula 150. The stiffening member can be secured to the optical fiber 138 using a suitable adhesive (e.g., glue, epoxy, etc.), mechanical connection, and/or combinations thereof. Similarly, the stiffening member can be secured to the handle 146 using a suitable adhesive (e.g., glue, epoxy, etc.), mechanical connection, and/or combinations thereof.

Generally, the actuator system 178 can be configured to move the EAP actuator 190 from a neutral position to one or more activated positions. As a result, the actuator system 178 can be likewise configured to move the distal end 180 of the optical fiber 138 from a neutral position to one or more activated positions. For example, FIG. 2 illustrates an embodiment where the neutral position of the optical fiber 138 can be coaxial with the longitudinal axis of the cannula 150. The actuator system 178 can be configured to move the distal section 198 of the EAP actuator 190 and, thereby, the distal end 180 of the optical fiber 138 from the position coaxial with the longitudinal axis to a first activated (as depicted in FIG. 3) and a second activated position (as depicted in FIG. 4). Current can flow through the electrical conductors 192, 194 and the EAP actuator 190 in a first direction to urge the EAP actuator 190 in direction 200 and, thereby, the distal end 180 of the optical fiber 138 in direction 204 towards the first activated position of FIG. 3. Current can flow through the electrical conductors 192, 194 and the EAP actuator 190 in the opposing direction to urge the EAP actuator 190 in direction 202 and, thereby, the distal end 180 of the optical fiber 138 in direction 206 towards the second activated position of FIG. 4.

By oscillating the optical fiber between the first and second activated positions illustrated in FIGS. 3 and 4, the imaging beam can be scanned across the target biological tissue, such as the retina. In some implementations, the actuator system 178 can be configured to oscillate the distal end 180 of the optical fiber 138 between the first and second activated positions within a frequency range between about 1 Hz and about 30 Hz, between about 5 Hz and 20 Hz, or between about 10 Hz and 15 Hz, although other frequency ranges, both larger and smaller, are contemplated.

The positions of the distal end 180 of the optical fiber 138 depicted in FIGS. 3 and 4 can also be the neutral position for the actuator system 178. In that regard, the distal end 180 of the optical fiber 138 can begin in the position of FIG. 3 or FIG. 4 and then move to the position of FIG. 4 or FIG. 3, respectively, upon energization of the EAP actuator 190. In such implementations, current can flow through the electrical conductors 192, 194 and the EAP actuator 190 in a manner to urge the EAP actuator 190 and, thereby, the distal end 180 of the optical fiber 138 towards the opposite position. By stopping the current and/or reversing the current, the EAP actuator 190 and the distal end 180 of the optical fiber 138 can be urged back towards the starting position. In that regard, the elastic force of the EAP actuator 190, the optical fiber 138, and/or the stiffening member can cause them to return to the original starting position. As discussed below, in some implementations the actuator system 178 can include one or more restoring elements to facilitate returning the EAP actuator 190 and the optical fiber 138 back to the starting position. The restoring element(s) can be mechanical (e.g., resiliently flexible elements) and/or electromagnetic.

FIG. 5 provides a stylized illustration of a cross-sectional view of the imaging probe 130 in accordance with another aspect of the present disclosure. The probe 130 of FIG. 5 includes many features similar to those discussed above that will not be repeated here for sake of brevity. The actuator system 178 of the probe 130 of FIG. 5 can include the EAP actuator 190 and a restoring element 214. The restoring element 214 can be configured to urge the EAP actuator 190 and, thereby, the optical fiber 138 back to a starting position. The starting position can be a position similar to the positions shown in any of FIGS. 2-4.

In the illustrated embodiment of FIG. 5, the restoring element 214 can be a flexible restoring element, such as a leaf spring. In that regard, a proximal section 216 of the restoring element 214 can be fixedly secured to the handle 146, while a distal section 218 of restoring element 214 can be configured to interface with the distal section 198 of the EAP actuator 190. In particular, as the distal section 198 of the EAP actuator 190 moves as a result of energizing the EAP actuator 190 the distal section 218 of the restoring element 214 can be correspondingly displaced. With the current to the EAP actuator 190 turned off (or reversed) the potential energy resulting from displacement of the distal section 218 of the flexible restoring element 214 can impart a restoring force on the EAP actuator 190 to cause it to return to its starting position.

FIG. 6 provides a stylized illustration of a cross-sectional view of the imaging probe 130 in accordance with another aspect of the present disclosure. The probe 130 of FIG. 6 includes many features similar to those discussed above that will not be repeated here for sake of brevity. The actuator system 178 can be similar to that of FIG. 5, but includes an alternative restoring element 224. In the illustrated embodiment of FIG. 6, the restoring element 224 can be a flexible restoring element, such as a coil spring. In that regard, a lower portion of the coil spring can be fixedly secured to the handle 146, while an upper portion of the coil spring can be configured to interface with the distal section 198 of the EAP actuator 190. In particular, as the distal section of the EAP actuator 190 moves as a result of energizing the EAP actuator 190 the coil spring will be correspondingly compressed or stretched. With the current to the EAP actuator 190 turned off (or reversed) the potential energy resulting from compression or stretching of the restoring element 224 will impart a restoring force on the EAP actuator 190 to cause it to return to its starting position.

Figure 7:
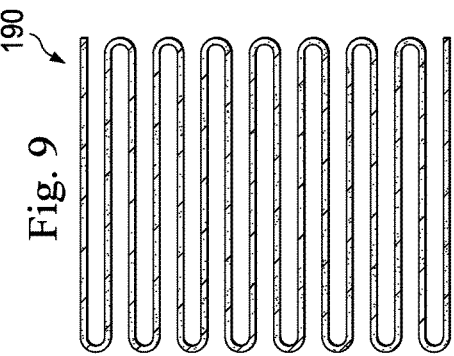
FIG. 7 provides a stylized illustration of a cross-sectional view of an electroactive polymer actuator.

FIG. 7 provides a stylized illustration of a cross-sectional view of the EAP actuator 190 in accordance with an aspect of the present disclosure. The EAP actuator 190 can include a sandwich structure that includes an EAP layer 230, conductive layers 232, and insulating layers 234. The conductive layers 232 can be electrically coupled to the electrical conductors 192, 194. As a result, electrical current can be passed through conductors 192, 194 to conductive layers 232 and through EAP layer 230. The direction and magnitude of the current can be controlled by the controller 126 to achieve a desired motion profile for the EAP actuator 190.

The conductive layers 232 of the EAP actuator 190 can be covered by the insulating layers 234. The insulating layers 234 can isolate the conductive layers 232 and/or the EAP layer 230 from the surrounding environment, including other features or structures of the probe 130. The insulating layers 234 can include one or more layers of insulating material, such as parylene or other suitable polymers to provide an insulating barrier. The insulating layers 234 can have a thickness of 100 microns or less, 50 microns or less, 10 microns or less, 5 microns or less, or 1 micron or less.

Figure 8:
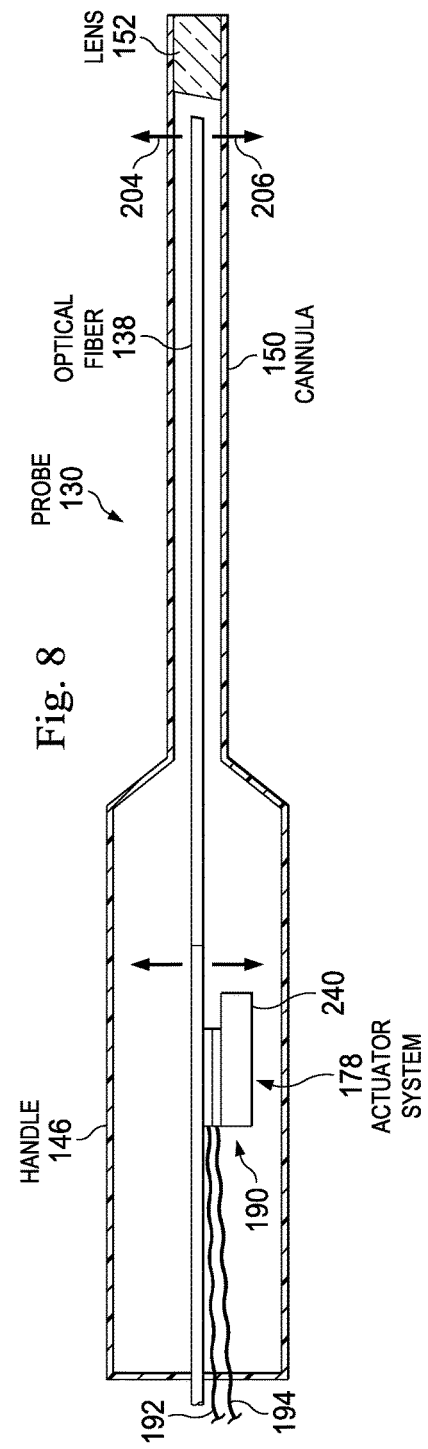
FIG. 8 provides a stylized illustration of a cross-sectional view of an imaging probe.

FIG. 8 provides a stylized illustration of a cross-sectional view of the imaging probe 130 in accordance with another aspect of the present disclosure. The probe 130 of FIG. 8 includes many features similar to those discussed above that will not be repeated here for sake of brevity. The actuator system 178 of the probe 130 of FIG. 8 can include the EAP actuator 190 and a shape-control element 240. The EAP actuator 190 can be configured to expand or shrink upon an electric stimulation of the EAP actuator 190 and shrink or expand, respectively, upon stopping or reversing the electrical stimulation of the EAP actuator. The EAP actuator 190 can be a stacked EAP. The stacked EAP can include an elongated EAP folded back-and-forth to form a layered structure (e.g., as shown in FIG. 9), a repeating electrically conductive layer—EAP layer—electrically conductive layer sandwich structure (e.g., as shown in FIG. 10), or a repeating EAP layer—electrically conductive layer sandwich structure (e.g., as shown in FIG. 11).

The shape-control element 240 can be configured to control a shape of the EAP actuator 190 during expansion and shrinking. For example, the shape-control element 240 can be a structure that maintains the EAP actuator 190 within a profile of the shape-control element 240. As a result, the shape-control element 240 can be utilized to ensure that the EAP actuator 190 expands and shrinks in the desired direction(s) during use. The shape-control element 240 can be a separate structure secured within the handle 146. The shape-control element 240 can be integrally formed as part of the handle 146. For example, an internal portion of the handle 146 can be sized and shaped to receive the EAP actuator 190 and serve as the shape-control element 240. Generally, the shape-control element 240 can have any shape suitable for controlling the shape of the EAP actuator 190 during expansion and shrinking to ensure that the EAP actuator 190 expands and shrinks in the desired direction(s), including geometrical, non-geometrical, symmetrical, non-symmetrical, continuous, and/or intermittent structures.

A proximal section of the optical fiber 138 can extend across and be secured to a top layer of the stacked EAP actuator 190 such that the optical fiber 138 moves with the top layer of the EAP actuator 190 in response to the application of an electric voltage to the EAP actuator 190. In that regard, the EAP actuator 190 can be configured to bias the optical fiber 138 and/or an associated stiffening member to one extreme of the desired motion profile of optical fiber 138 (e.g., the position of either FIG. 3 or FIG. 4). Additional spring force can be provided using one or more flexible or elastic components, such as leaf springs, coil springs, or other suitable flexible members, to urge the optical fiber 138 to the desired starting position. Biasing the optical fiber 138 and/or the stiffening member in this manner can allow activation of the EAP actuator 190 to move the optical fiber 138 and/or stiffening member in a single direction to the other extreme of the desired motion profile to scan the imaging beam across the proximal face 182 of the lens 152. De-activating or reversing the current causes the EAP actuator 190 and the optical fiber 138 to return to the starting position. The starting, biased position of the optical fiber 138 can be the position of FIG. 3 such that activation of the EAP actuator 190 causes the EAP actuator 190 to contract or shrink, thereby moving the optical fiber 138 to the position of FIG. 4. Alternatively, the starting, biased position of the optical fiber 138 can be the position of FIG. 4 such that activation of the EAP actuator 190 causes the EAP actuator 190 to expand, thereby moving the optical fiber 138 to the position of FIG. 3.

Figure 9:
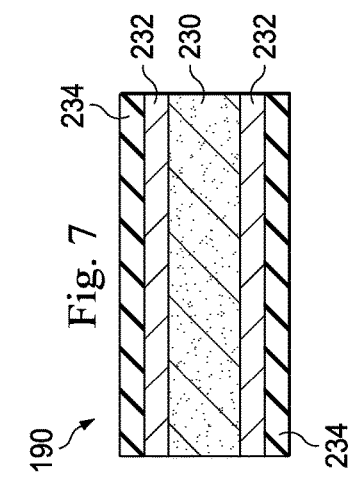
FIG. 9 provides a stylized illustration of a side view of an electroactive polymer actuator.

FIG. 9 provides a stylized illustration of a side view of an electroactive polymer actuator 190 in accordance with another aspect of the present disclosure. The EAP actuator 190 of FIG. 9 can include a stacked EAP. In particular, the EAP actuator 190 of FIG. 9 can include an elongated strip of EAP folded back-and-forth on itself to form a multi-layered structure. The elongated strip of EAP can be folded back-and-forth to form between 2 and 100 layers, between 10 and 50 layers, or between 15 and 25 layers. The elongated strip of EAP can have conductive layers on its opposing top and bottom surfaces and an outer insulating covering to electrically isolate the EAP and conductive layers from surrounding components of the probe 130 (e.g., similar to the EAP structure of FIG. 7).

FIG. 10 provides a stylized illustration of a cross-sectional view of an electroactive polymer actuator 190 in accordance with another aspect of the present disclosure. The EAP actuator 190 of FIG. 10 can include a stacked EAP. In particular, the EAP actuator 190 of FIG. 10 can include a repeating pattern of electrically conductive layer 232—EAP layer 230—electrically conductive layer 232 sandwich structure. In that regard, the top conductive layer 232 associated with one EAP layer 230 can contact the bottom conductive layer 232 associated with the above EAP layer 230. As a result, these adjacent conductive layers 232 can form a single electrical contact. By alternating which of the electrical conductor 192 or 194 can be electrically coupled to the pairs of adjacent conductive layers 232, the alternating pairs of adjacent conductive layers 232 can form parallel circuits that can be the anode and cathode of the EAP stack. For example, in the illustrated embodiment of FIG. 10, the bottom most conductive layer 232 of the EAP stack can be electrically coupled to electrical conductor 194, the next pair of adjacent conductive layers 232 can be electrically coupled to electrical conductor 192, the next pair of adjacent conductive layers 232 can be electrically coupled to electrical conductor 194, and the top most conductive layer 232 of the EAP stack can be electrically coupled to electrical conductor 192. In this manner, the electrically conductive layers 232 can be configured to receive an electric voltage in a spatially alternating manner, or in general, configured to be electrically stimulated in a spatially alternating manner. This approach can be repeated for any number of layers. Further, while the embodiment of FIG. 10 illustrates each of the adjacent conductive layers 232 having a separate lead or connection to the respective electrical conductor 192, 194, a single lead or connection can be utilized to electrically couple both of the adjacent conductive layers 232 to the appropriate electrical conductor 192, 194.

FIG. 11 provides a stylized illustration of a cross-sectional view of an electroactive polymer actuator 190 in accordance with another aspect of the present disclosure. The EAP actuator 190 of FIG. 11 can include a stacked EAP. In particular, the EAP actuator 190 of FIG. 11 can include a repeating pattern of electrically conductive layer 232—EAP layer 230 sandwich structure. In these sandwich structures the conductive layers 232 can be coupled to the EAP layers 230 above and below. By alternating which of the electrical conductors 192 or 194 the conductive layers 232 are electrically coupled to, the alternatingly coupled conductive layers 232 can form parallel circuits that can be the anode and cathode of the EAP stack. For example, in the illustrated embodiment of FIG. 11, the bottom most conductive layer 232 of the EAP stack can be electrically coupled to electrical conductor 194, the next conductive layer 232 above can be electrically coupled to electrical conductor 192, the next conductive layer 232 above can be electrically coupled to electrical conductor 194, and the top most conductive layer 232 of the EAP stack can be electrically coupled to electrical conductor 192. In this manner, the electrically conductive layers 232 can be configured to receive an electric voltage in a spatially alternating manner. More generally, the electrically conductive layers 232 can be configured to be electrically stimulated in a spatially alternating manner, wherein the electrical stimulation can include an application of a voltage, an electric field, or a current, as discussed above. This approach can be repeated for any number of layers.

The motion profiles discussed in the context of the actuator systems above focused on linear displacement of the optical fiber 138 within cannula, which can be utilized to produce a corresponding linear scan of the imaging beam across the target biological tissue. In other embodiments, the actuator system can include one or more additional EAP actuator 190 besides the above described EAP actuator 190, oriented at different angles, that can be selectively energized to scan the optical fiber 138 and the imaging beam across a two-dimensional scanning pattern. The originally described EAP actuator 190 can be configured to impart motion to the optical fiber 138 along a first axis and the one or more additional EAP actuator 190 can be configured to impart motion to the optical fiber 138 along one or more additional axis that are different from the first axis. In some embodiments there can be one additional EAP actuator 190, with the one additional axis being perpendicular to the first axis to impart motion to the optical fiber 138 along two perpendicular axes. In other embodiments, there can be two additional EAP actuators 190, positioned, e.g., at 120 degrees from each other and the original EAP actuator 190, and configured to impart motion to the optical fiber 138 along axes that form 120 degrees with each other. The two-dimensional scanning pattern can include a spiral, a raster, a constant-radius asterisk, a multiple-radius asterisk, a multiply folded path, other two-dimensional scan patterns, and/or combinations thereof.

Embodiments as described herein may provide an imaging probe having an actuator that utilizes a EAP actuator to impart motion to an optical fiber positioned within the imaging probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic imaging apparatus, comprising:
an optical probe having
a handle, sized and shaped for handheld grasping by a user;
a cannula, coupled to the handle, the cannula sized and shaped for insertion into an eye to be treated; and
an optical fiber positioned at least partially within the cannula of the optical probe, the optical fiber configured to receive an imaging light from an imaging light source and guide the imaging light to an optical element within the cannula of the optical probe;
an electroactive polymer (EAP) actuator system configured to impart motion to the optical fiber, the EAP actuator system including an EAP actuator positioned within the handle of the optical probe and at least partially surrounding the optical fiber, the optical fiber extending past a distal end of the EAP actuator, and wherein the EAP actuator is configured to strain when the EAP actuator is electrically stimulated in an alternating manner to impart a resulting oscillatory motion to the optical fiber; and
a mechanical restoring element configured to counteract the motion imparted to the optical fiber by the EAP actuator, the mechanical restoring element having proximal and distal ends, a distal end of the mechanical restoring element coupled to a distal end of the EAP actuator, and a proximal end of the mechanical restoring element coupled to the handle.

2. The apparatus of claim 1, wherein:
the EAP actuator system is configured to impart amplified motion to a distal section of the optical fiber.

3. The apparatus of claim 2, wherein:
the optical fiber is coupled to the EAP actuator such that motion imparted to the distal end of the optical fiber is amplified relative to the movement of the EAP actuator.

4. The apparatus of claim 3, wherein:
the motion imparted to the distal end of the optical fiber is at least 10% greater than the movement of the distal end of the EAP actuator.

5. The apparatus of claim 3, wherein:
the distal end of the EAP actuator is configured to move relative to the handle upon an electrical stimulation of the EAP actuator, wherein
the electrical stimulation can include an application of at least one of a voltage, electric field, and current to the EAP actuator.

6. The apparatus of claim 5, wherein:
a proximal end of the EAP actuator is affixed to the handle.

7. The apparatus of claim 6, wherein:
the distal end of the EAP actuator is configured to at least one of bend and curl relative to the proximal end upon application of the electric voltage to the EAP actuator.

8. The apparatus of claim 3, wherein:
the electroactive polymer actuator is positioned at least partially within the cannula.

9. The apparatus of claim 3, wherein:
the EAP actuator is configured
to expand upon an electric stimulation, and
to shrink upon stopping or reversing the electric stimulation.

10. The apparatus of claim 3, wherein:
the EAP actuator is configured
to shrink upon an electric stimulation, and
to expand upon stopping or reversing the electric stimulation.

11. The apparatus of claim 3, wherein the EAP actuator system further comprises:
a shape-control element configured to control a shape of the EAP actuator during expansion and shrinking.

12. The apparatus of claim 3, wherein:
the EAP actuator is a stacked EAP actuator.

13. The apparatus of claim 12, wherein:
the stacked EAP actuator comprises an elongated EAP folded back-and-forth to form a multi-layered structure.

14. The apparatus of claim 12, wherein:
the stacked EAP actuator comprises a repeating EAP layer—electrically conductive layer sandwich structure; and
the electrically conductive layers are configured to receive an electric stimulation in a spatially alternating manner.

15. The apparatus of claim 12, wherein:
the stacked EAP actuator comprises a repeating electrically conductive layer—EAP layer—electrically conductive layer sandwich structure; and
the electrically conductive layers are configured to receive an electric stimulation in a spatially alternating manner.

16. The apparatus of claim 1, wherein the EAP actuator comprises:
an EAP sandwich structure, comprising
an EAP layer;
a first insulating layer;
a second insulating layer;
a first electrically conductive layer positioned between the EAP layer and the first insulating layer; and a second electrically conductive layer positioned between the EAP layer and the second insulating layer.

17. The apparatus of claim 1, wherein the EAP actuator comprises:
at least one of an ionic EAP and a dielectric EAP.

18. The apparatus of claim 1, wherein:
the cannula and a distal section of the handle are removably coupled to a proximal section of the handle such that the cannula and the distal section of the handle are disposable.

19. The apparatus of claim 1, wherein:
the cannula is fixedly secured to the handle and a proximal section of the handle includes a connector configured to selectively couple the optical probe to a cable.

20. The apparatus of claim 19, wherein:
the optical probe is disposable.

21. The apparatus of claim 1, wherein:
the restoring element is a flexible restoring element.

22. The apparatus of claim 1, wherein:
the optical element comprises at least one of a lens and a gradient index (GRIN) lens.

23. The apparatus of claim 1, wherein:
the optical element is mechanically coupled to a distal end of the optical fiber so that the optical element moves with the distal end of the optical fiber.

24. The apparatus of claim 1, wherein:
the EAP actuator system is configured to impart motion to the optical fiber to scan the imaging light over a two-dimensional scanning pattern.

25. The apparatus of claim 24, wherein:
the two dimensional scanning pattern comprises at least one of a spiral, a raster, a constant-radius asterisk pattern, a multiple-radius asterisk pattern, and a multiply folded path.

26. The apparatus of claim 24, wherein:
the EAP actuator system comprises one or more additional EAP actuator, wherein the EAP actuator is configured to impart motion to the optical fiber along a first axis and the one or more additional EAP actuator is configured to impart motion to the optical fiber along one or more additional axis different from the first axis.

27. The apparatus of claim 1, wherein the EAP actuator is configured move the optical fiber between a first position and a second position opposite the first position in an oscillatory manner when current is applied to the EAP actuator in a first direction and a second direction opposite the first direction in an alternating manner.

28. The apparatus of claim 1, wherein EAP actuator and the optical fiber extend longitudinally within the optical probe, and wherein the EAP actuator is directly in contact with the optical fiber along a length of the optical fiber.

29. An ophthalmic imaging system, comprising:
an imaging light source configured to generate an imaging light;
an optical guide in optical communication with the imaging light source, the optical guide configured to receive the generated imaging light from the imaging light source; and
a probe in optical communication with the optical guide, the probe including
a handle sized and shaped for handheld grasping by a user; and
a cannula coupled to the handle, the cannula sized and shaped for insertion into an eye to be treated;
an optical fiber positioned at least partially within the optical probe, the optical fiber configured to receive the imaging light from the optical guide and guide the imaging light to an optical element positioned within the cannula of the optical probe;
a stiffening member positioned around the optical fiber and extending along the optical fiber entirely within the handle;
an electroactive polymer (EAP) actuator system configured to impart motion to the optical fiber, the EAP actuator system an EAP actuator positioned within the optical probe and in sustained direct contact with the stiffening member at a proximal end of the optical fiber while a distal end of the optical fiber extends past a distal end of the EAP actuator, and wherein the EAP actuator is configured to strain when the EAP actuator is electrically stimulated in an alternating manner to impart oscillatory motion to the stiffening member and the optical fiber when the EAP actuator is electrically stimulated in an alternating manner, wherein the stiffening member is biased to cause the optical fiber to rest in a starting position before electrical stimulation with a distal end of the optical fiber at a first extreme position of the oscillatory motion; and
a mechanical restoring element configured to counteract the motion imparted to the optical fiber by the EAP actuator, the mechanical restoring element having proximal and distal ends, a distal end of the mechanical restoring element coupled to a distal end of the EAP actuator, and a proximal end of the mechanical restoring element coupled to the handle.

30. The ophthalmic imaging system of claim 29, further comprising:
a controller in communication with the light source, the controller configured to control actuation of the imaging light source for an optical coherence tomography (OCT) imaging procedure.

31. The ophthalmic imaging system of claim 30, wherein:
the controller is further configured to process data obtained by the probe and output imaging data to a display in communication with the controller.

32. A method of imaging an ophthalmic target with an imaging probe, comprising:
guiding an imaging light to an optical fiber positioned within a cannula of the imaging probe with an optical guide, the optical fiber having a stiffening member positioned around the optical fiber and extending along the optical fiber entirely within the handle;
biasing the stiffening member to cause the optical fiber to rest in a starting position;
focusing the imaging light onto the ophthalmic target with an optical element positioned within the cannula of the imaging probe;
scanning the focused imaging light through a scanning pattern by moving a distal end of the optical fiber in an oscillatory manner by straining an electroactive polymer (EAP) actuator by alternatingly applying an electric stimulation to the EAP actuator positioned within the imaging probe and in sustained direct contact with a proximal end of the optical fiber, wherein the starting position before electrical stimulation comprises a position with a distal end of the optical fiber at a first extreme position of the oscillatory motion; and
returning the optical fiber to an original position using a mechanical restoring element configured to counteract the motion imparted to the optical fiber by the EAP actuator, the mechanical restoring element having proximal and distal ends, a distal end of the mechanical restoring element coupled to a distal end of the EAP actuator, and a proximal end of the mechanical restoring element coupled to the handle.

\* \* \* \* \*